United States Patent [19]

Godfrey

[11] 4,283,339

[45] Aug. 11, 1981

[54] PREPARATION OF DIOXANE AND CO-PRODUCTS

[75] Inventor: Norman B. Godfrey, Austin, Tex.

[73] Assignee: Highland Resources, Inc., Houston, Tex.

[21] Appl. No.: 53,558

[22] Filed: Jun. 29, 1979

[51] Int. Cl.³ .......................................... C07D 319/10
[52] U.S. Cl. ................................. 260/340.6; 546/254
[58] Field of Search ...................................... 260/340.6

[56] References Cited

U.S. PATENT DOCUMENTS 4,007,095   2/1977   Wolf et al. ....................... 260/340.6

FOREIGN PATENT DOCUMENTS 740423   11/1955   United Kingdom .

OTHER PUBLICATIONS

Inoue et al., J. Chem. Soc., Japan, (1955).
Fieser, Experiments in Organic Chemistry, p. 368–369.
Chem. Abstracts 50, 15600, (1956).
Chem. Abstracts 33, 1663, (1939).
Chem. Abstracts 44, 2986, (1950).
Chem. Abstracts 47, 3311, (1953).
Chem. Abstracts 49, 2108, (1955).
Chem. Abstracts 50, 13024, (1956).

*Primary Examiner*—Ethel G. Love
*Attorney, Agent, or Firm*—Finnegan, Henderson, Farabow, Garrett & Dunner

[57] ABSTRACT

Dioxane is prepared by reaction of polyethylene glycols in a catalytically active liquid reaction medium comprising a mixture of partial phosphate esters of a polyethylene glycol, and ammonium salts of partial esters of a polyethylene glycol. Along with dioxane, valuable co-products, including the compound 5-ethyl-2-methylpyridine, are formed from which the dioxane is readily separated in highly pure form. The catalytically active liquid reaction medium is derived from the reaction of ammonium dihydrogen phosphate with a polyethylene glycol at temperatures preferably in the range from 190° to 225° C. Temperatures of reaction between the polyethylene glycol and the catalytically active liquid reaction medium to form the dioxane and co-products are preferably in the range of from about 225° C. to about 275° C.

22 Claims, No Drawings

PREPARATION OF DIOXANE AND CO-PRODUCTS

This invention relates to the preparation of useful organic chemical compounds. More particularly, the present invention relates to the preparation of dioxane, a highly versatile liquid organic compound, and valuable by-products, including 5-ethyl-2-methylpyridine which can be readily separated from the dioxane.

BACKGROUND OF THE INVENTION

The dioxane which is the subject of this invention is the ordinary dioxane of commerce, otherwise known as 1,4-dioxane and p-dioxane, and has the formula:

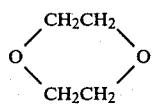

It has a boiling point of about 101° C. and a melting point of about 12.5° C. It is thus liquid at typical ambient temperatures.

Dioxane is a widely used chemical material. It is soluble in water, and finds extensive utility as an industrial solvent for a large number of chemical substances covering a wide range of polarities. For example, it readily dissolves fats, waxes, natural and synthetic resins, cellulose ethers, and lacquers.

Heretofore, dioxane has been prepared by the acid-catalyzed dehydration of polyethylene glycols. Strong acid catalysts, such as sulfuric acid and sulfonated cation-exchange resins, have been disclosed as suitable for the synthesis of dioxane from polyethylene glycols. Unfortunately, prior methods of dioxane synthesis result in the co-production of significant amounts of an isomeric by-product, 2-methyl-1,3-dioxolane. Purification of the dioxane is difficult, involving tedious and expensive measures for the removal of the isomer. A common method includes refluxing with hydrochloric acid in a current of nitrogen to remove the 2-methyl-1,3-dioxolane, drying with potassium hydroxide, refluxing with metallic sodium, and finally distilling from sodium.

For some uses, the purity of the dioxane must be very high. For example, when used in spectroscopic and scintillation analysis, or as a reaction medium for organometallic chemistry, the dioxane concentration must be as close to 100% as possible. The presence of the isomeric dioxolane is especially a problem when high purity dioxane is sought for these applications.

It would therefore be desirable to have a procedure for the preparation of dioxane which does not involve the formation of the troublesome isomeric by-product and which instead produces a crude reaction product from which the dioxane can be isolated relatively easily to achieve a high purity product. It has now been found that dioxane can be synthesized from polyethylene glycols in accordance with the present invention as hereinafter described, without the formation of the isomer 2-methyl-1,3-dioxolane. By the invention herein, dioxane is formed along with co-products from which the dioxane can be readily separated and recovered in highly pure form.

One of the by-products of the novel process of this invention is the compound 5-ethyl-2-methylpyridine having the formula:

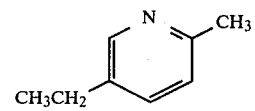

This alkylpyridine is useful in the production of the important B-complex vitamin niacin and in the production of oil-resistant synthetic rubbers. 5-Ethyl-2-methylpyridine has previously been prepared from acetaldehyde or paraldehyde and ammonia. Hence, the present invention also provides a novel method of making this valuable pyridine derivative which can be separated from the dioxane and isolated in a relatively pure state.

Accordingly, a principal object of the present invention is to provide a method for the preparation of dioxane and valuable co-products. A further object is to provide a method for preparing dioxane in high purity without having to utilize difficult purification techniques.

Another object of the present invention is to provide a composition containing dioxane and 5-ethyl-2-methylpyridine. A further object of the present invention is to provide a method of treating a composition containing dioxane and 5-ethyl-2-methylpyridine to isolate these respective compounds in relatively pure form.

Still another object of the present invention is to provide a reaction medium for the conversion of polyethylene glycols to dioxane and 5-ethyl-2-methylpyridine.

These and other objects of the present invention which will be apparent hereinafter are obtained by the present invention which resides in the compositions, compounds, materials and processes described herein.

SUMMARY OF THE INVENTION

In a broad sense, the present invention provides a method for the preparation of a composition comprising dioxane and 5-ethyl-2-methylpyridine by introducing into a heated reaction zone a liquid polyethylene glycol having the formula $H(OCH_2CH_2)_nOH$, wherein n is at least 2, in the presence of a liquid reaction medium comprising a mixture of partial phosphate esters and their ammonium salts, and recovering by distillation from the reaction zone a crude product mixture comprising dioxane, 5-ethyl-2-methylpyridine and water. The polyethylene glycol or a mixture of polyethylene glycols desirably is soluble in the reaction medium. A suitable temperature range for conducting the reaction is from about 225° C. to about 275° C.

The method of the present invention is especially suited for continuous processing by continuously feeding a liquid polyethylene glycol to the heated reaction zone. The reaction medium may be replenished in situ to permit the overall process to be effected on a continuous basis.

The reaction medium is a complex mixture comprising partial phosphate esters of polyethylene glycol and their ammonium salts. It is suitably prepared by the reaction of ammonium dihydrogen phosphate with a liquid polyethylene glycol having the formula $H(OCH_2CH_2)_nOH$, where n is at least 2, preferably not greater than 7, and more preferably not greater than 4. A mixture of polyethylene glycols may also be used, wherein n has more than one of these values. Crystalline ammonium dihydrogen phosphate may be used in the reaction in its commercially available crystalline form. It may also be prepared economically in the reaction zone by partially neutralizing phosphoric acid with one equivalent of ammonia or ammonium hydroxide. The mole ratio of ammonium dihydrogen phosphate to polyethylene glycol may be in the range of from about 0.8:1 to about 12:1, or more preferably from about 2:1 to about 4:1.

The reactants are heated and stirred at temperatures above the melting point of ammonium dihydrogen phosphate (which is about 190° C.), while generating a colorless volatile reaction product mixture comprising water and ammonia, or ammonium hydroxide. The temperature is preferably raised gradually to about 225° C., and then held steady until the rate of formation of the colorless distillate slackens. At this point, ester formation has proceeded to a sufficient degree to provide a satisfactory reaction medium for the main stage of the process. It then has sufficient solvent capacity for polyethylene glycol to ensure a smooth conversion of the latter to the desired reaction products.

Preferably, the polyethylene glycol feed is introduced continuously into the reaction zone containing the reaction medium prepared as above, at a temperature in the range of from about 225° C. to about 275° C., or more preferably between 240° C. and 260° C. The reaction zone need not be maintained at a constant temperature; the temperature may vary over the desired range during the course of the reaction. A crude volatile product mixture is continuously formed, and condenses on cooling to an amber-colored distillate comprising mainly dioxane, 5-ethyl-2-methylpyridine, water, and a little ammonia.

In accordance with the present invention, a polyethylene glycol having the formula H(OCH$_2$CH$_2$)$_n$OH, wherein n is at least 2, is heated in the reaction medium for a time sufficient to produce an overhead volatile composition comprising dioxane, 5-ethyl-2-methylpyridine, and other co-products which can be condensed by cooling and then collected. Preferably, the polyethylene glycol is selected from the group consisting of diethylene glycol, triethylene glycol, tetraethylene glycol and mixtures thereof. Mixtures of polyethylene glycols having an average molecular weight in the range of from about 200 to about 300 are also useful in the practice of the method of this invention.

In keeping with the concept of the present invention, high purity dioxane can be obtained by treating the condensed distillate with a suitable desiccant to form an organic layer and an aqueous layer, separating the organic layer, drying the organic layer, and fractionally distilling the dried organic layer. Dioxane, having a boiling point of about 101° C., and 5-ethyl-2-methylpyridine, having a boiling point of about 178° C., are readily separable by fractional distillation because of the wide disparity in boiling points.

Through the practice of this invention, dioxane having a purity of 99.8% and above is obtainable. The difficulties involved in separation of the dioxolane isomer do not arise. Instead, 5-ethyl-2-methylpyridine is formed and is readily separable and recoverable.

The general description of the invention above, along with the more detailed description of particular and preferred embodiments of the invention hereinafter, serve to illustrate the various aspects of this invention.

DETAILED DESCRIPTION OF EMBODIMENTS OF THE INVENTION

The synthesis of dioxane in accordance with the present invention involves the conversion of the polyethylene glycol starting material into the cyclic diether of ethylene glycol. Any liquid polyethylene glycol which is soluble in the liquid reaction medium described above can be used as the feed material in the process of the present invention.

Polyethylene glycols are the ether diol addition reaction products of ethylene oxide and ethylene glycol. Suitable feed polyethylene glycols useful in the practice of the present invention are liquid polyethylene glycols having the formula H(OCH$_2$CH$_2$)$_n$OH, wherein n is at least 2. Preferably, n is in the range of from 2 to 12, and most preferably, n is from 2 to 7. The molecular weights of polyethylene glycols wherein n is from 2 to 7 range from about 106 to about 326. Mixtures of polyethylene glycols having an average molecular weight in this range may desirably be employed.

Specific preferred polyethylene glycols for use as the starting material in the process of the present invention include diethylene glycol, triethylene glycol, tetraethylene glycol, mixtures thereof, and mixtures of polyethylene glycols wherein the average molecular weight is in the range 200 to about 300. Suitable polyethylene glycol materials are PEG-200, a commercially available mixture of polyethylene glycols having an average molecular weight of approximately 200, and PEG-300, a commercially available mixture of average molecular weight of about 300. Other low molecular weight mixtures of polyethylene glycols known as "glycol bottoms" are still residues produced from the distillation of lower glycols and represent available, useful feed materials for this invention. The polyethylene glycol used as feed material may be the same as or different from the one used in forming the reaction medium.

The precise composition of the reaction medium is presently uncertain. In view of its mode of formation by the reaction of polyethylene glycol with ammonium dihydrogen phosphate, it is believed to contain phosphate ester groups, acidic hydroxyl groups, anionic substituted phosphate groups, and ammonium ions. The principal molecular species present may be represented by the general formula:

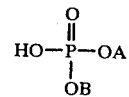

where, in different components of the mixture, A may be H or NH$_4$, and B may be (CH$_2$CH$_2$O)$_n$H or

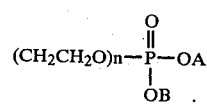

The moderately acidic ester-acid-salt mixture is an amber-colored liquid at the temperature of use. If cooled to room temperature, it sets to a soft, resinous solid. In view of its complex composition, the mixture is best characterized by its mode of formation; however, equivalent compositions prepared by other means are also contemplated as within the scope of the present invention.

In a less preferable mode of formation of the catalytic reaction medium, ammonium dihydrogen phosphate may be preheated to a temperature above about 225° C., and a polyethylene glycol feed material may then be added to the molten salt. In this mode of operation, the commencement of product formation overlaps with ester formation, and is somewhat unpredictable. It is generally accompanied by a sudden rise in temperature and in rate of distillation. The preferred mode of operation, as previously described, leads to a cleaner, smoother, faster, and more easily controlled reaction.

In accordance with the preferred embodiment of the present invention, a reaction medium is first prepared by heating and stirring a mixture of diethylene glycol and ammonium dihydrogen phosphate in a mole ratio from about 2:1 to about 4:1, at temperatures above about 190° C. and gradually rising to about 225° C., while distilling off a colorless liquid volatile product comprising mainly dilute ammonium hydroxide. A feed composition comprising one or more liquid polyethylene glycols having the formula $H(OCH_2CH_2)_nOH$, where n may range from 2 to about 7, optionally mixed with ammonia or ammonium hydroxide up to the extent of about 4 percent as $NH_3$, is then added continuously at temperatures from about 240° C. to about 260° C., while distilling an amber-colored crude product mixture comprising dioxane, 5-ethyl-2-methylpyridine, and water. The rate of addition of the feed material is preferably about equal to the rate of formation of crude product, which depends on the temperature and the amount of the reaction medium. The duration of a run may be as long as desired, within limits set by the eventual formation of excessive amounts of tarry non-volatile by-products. Ammonia present in the reaction medium in combined form becomes depleted by the formation of the pyridine derivative, and may be replaced preferably by continuous addition in mixture with the feed material, as above.

In keeping with the concept of the present invention, dioxane and 5-ethyl-2-methylpyridine may be recovered from the crude distillate, which also contains water and small amounts of ammonia. Since both main products form azeotropes, or constant-boiling mixtures, with water, it is necessary to separate the water from the organic materials prior to distillation. As embodied herein, the crude distillate may initially be separated into an organic layer and an aqueous layer by the addition of a suitable desiccant. Effective desiccants for this purpose include soluble, strongly alkaline inorganic materials such as potassium hydroxide, sodium hydroxide, and potassium carbonate. Preferably potassium hydroxide is used, for example in the form of pellets or flakes. The amount of the desiccant is not critical, but desirably is sufficient to bring about complete separation of the organic constituents of the crude distillate. Suitable amounts of potassium hydroxide include from about 30 to about 70 percent of the weight of the crude distillate.

After dissolution of the desiccant in the crude distillate, a heavy aqueous layer settles out and is separated from the organic layer. Preferably, the organic layer is further dried by contact with a desiccant, for example potassium hydroxide in amounts of from about 4 to about 10 percent of the organic layer. The dried organic layer is a liquid composition comprising principally a mixture of dioxane and 5-ethyl-2-methylpyridine. The predominant component is dioxane. Typically the weight ratio of dioxane to 5-ethyl-2-methylpyridine ranges from about 5:1 to about 20:1.

In accordance with the present invention as embodied herein, the dioxane is separated from the dried liquid product composition by fractional distillation. The dioxane fraction is collected at a distillation temperature of approximately 101° C. Typically, the recovered dioxane fraction has a dioxane content of at least about 99.8 percent by weight. By the method of the present invention, purity of the dioxane fraction in excess of 99.9 percent is attainable by a single distillation.

After the dioxane fraction is distilled off, continued heating and distillation of the residual composition at about 178° C. produces a fraction which contains predominantly 5-ethyl-2-methylpyridine. Typically, the recovered high-boiling fraction contains at least about 96 percent by weight of 5-ethyl-2-methylpyridine. The fraction may be further purified by redistillation. It is expected that equally good separation of the two products can be attainable by continuous distillation, as for example by the use of bubble towers.

The invention will now be illustrated by the following examples. The examples are not intended to be limiting of the scope of the present invention. In conjuction with the general and detailed descriptions above, the examples provide further understanding of the present invention. In the examples, percentages are weight percentages and all distillation temperatures are uncorrected.

EXAMPLE 1

Into a reaction flask fitted with a stirrer, thermometer, dropping funnel, and distillation head connected to a water-cooled condenser was placed 115.7 g 85% phosphoric acid. A mixture of 65.2 g 28% ammonium hydroxide and 51.1 g diethylene glycol was added with stirring over a five-minute period. Power to the heating mantle was then turned on. The pot temperature was gradually raised to 225° C., while a fore-run distilled, consisting principally of water and a little ammonia. The liquid residue in the pot comprised a reaction medium for the feed polyethylene glycol.

Dropwise addition of diethylene glycol into the reaction medium was then started from the feed funnel, 54.1 g being added over a three-hour period at temperatures between 225° C. and 250° C. A clear, amber-colored distillate was collected over this period, amounting to 93.2 g.

Combined prerefrigerated crude products from this and another similar run, amounting to 145.6 g, were shaken with 100 g potassium hydroxide pellets until the latter were completely dissolved. An organic upper layer weighing 80 g was separated, further dried by contact with solid potassium hydroxide, and distilled through a ten-inch column of stainless steel protruded packing. A fraction weighing 44.8 g was collected at 100°–101° C. Analysis of the fraction by gas chromatography showed that it had a 99.9% content of dioxane. Another fraction distilling at 173°–175° C., weighing 9.9 g, contained 96.8% 5-ethyl-2-methylpyridine and 2.3% dioxane plus small amounts of other constituents.

EXAMPLE 2

Into a reaction flask as in Example 1 was placed 148 g ammonium dihydrogen phosphate. This was melted and heated with stirring to 265° C. while a fore-run of 8.1 g dilute ammonium hydroxide distilled. An initial charge of 17.6 g triethylene glycol was added rapidly to the reaction zone, followed by 48.9 g added dropwise at reaction temperatures between 255° C. and 274° C. over a three-hour period. The crude distillate, weighing 58.1 g, was dried and distilled as in Example 1, yielding a main product fraction which assayed 99.9% dioxane. In this case, a further fraction collected at 103°-174° C. contained 84.7% dioxane, 13.7% 5-ethyl-2-methylpyridine, plus small amounts of other pyridine derivatives and other compounds.

EXAMPLE 3

A run was made similar to Example 2 employing 214 g ammonium dihydrogen phosphate and using as the feed polyethylene glycol, 109.5 g PEG-200. The duration of the run was 3¼ hours at reaction temperatures between 245° C. and 260° C. The main product fraction weighed 23 g and showed a purity by gas chromatography of 99.95% dioxane.

EXAMPLE 4

120 g ammonium dihydrogen phosphate and 40 g diethylene glycol were weighed into a reaction flask and heated with stirring until the temperature of the fluid mixture reached 225° C. During this step a colorless distillate weighing 15.1 g was collected. The liquid residue in the reaction flask constituted a reaction medium.

An additional 100.8 g diethylene glycol were added dropwise to the reaction medium during 3 hours, 21 minutes at reaction temperatures predominantly in a range from 240° C. to 245° C. During this step, a light yellow distillate weighing 99 g was collected.

The distillate was treated with 39 g potassium hydroxide in two stages, yielding 53.6 g dry organic layer. On fractionation, the organic layer gave a main fraction of highly pure dioxane distilling between 100° C. and 100.5° C. which weighed 40.8 g. This represents a 49% yield of pure dioxane, based on diethylene glycol fed during the reaction step, or 35% on total diethylene glycol.

EXAMPLE 5

This example illustrates the presently preferred mode of practicing the invention.

A reaction medium was prepared by the reaction of 115 g (1.08 mole) diethylene glycol and 106 g (1.07 mole) ammonium dihydrogen phosphate with stirring and heating at temperatures rising from 194° to 226° C. over 30 minutes, while 33 g of colorless distillate was collected. A feed mixture was prepared from 111 g "Glycol Bottoms" (still residues from the distillation of ethylene glycol and diethylene glycol from a crude reaction product of ethylene oxide with water), mixed with 14 g concentrated ammonium hydroxide. This was fed continuously over a 2½ hour period to a reaction flask containing the reaction medium maintained at temperatures between 238° and 260° C. Heating and distillation were continued for another 13 minutes thereafter.

The amber-colored crude distillate collected during the run was treated with 51 g potassium hydroxide, and the aqueous layer which separated was drawn off with a separatory funnel. The organic upper layer was further dried by contact overnight with another 7 g portion of potassium hydroxide. The dried organic layer, amounting to 92 g, was fractionally distilled to recover a pure dioxane fraction at 100°-101° C. weighing 70 g.

Further distillation up to a head temperature of 170° C. yielded a high-boiling fraction comprising a mixture of dioxane and 5-ethyl-2-methylpyridine, weighing 7 g.

The scope of the present invention is not limited by the description and examples herein, and modifications can be made without departing from the spirit of the invention. For example, compounds other than dioxane and 5-ethyl-2-methylpyridine can be recovered from still residues remaining after the distillation of 5-ethyl-2-methylpyridine. Other modifications, adaptations and uses within the scope and spirit of this invention will occur to those skilled in the art.

What is claimed is:

1. A method of making dioxane comprising the steps of:
   (a) providing a reaction zone at temperatures in the range of from about 225° C. to about 275° C. containing a reaction medium comprising a mixture of partial phosphate esters of a polyethylene glycol and ammonium salts of partial esters of a polyethylene glycol; and
   (b) reacting a liquid polyethylene glycol in the reaction zone to form dioxane.

2. A method according to claim 1 wherein the liquid polyethylene glycol in step (b) comprises one or more members of the class of polyethylene glycols having the formula $H(OCH_2CH_2)_nOH$, wherein n is at least 2.

3. A method according to claim 1 wherein the reaction medium is formed by heating a mixture of ammonium dihydrogen phosphate and a liquid polyethylene glycol while distilling therefrom a mixture of water and ammonia.

4. A method of making dioxane comprising the steps of:
   (a) heating in a reaction zone a mixture of ammonium dihydrogen phosphate and a liquid polyethylene glycol, while distilling therefrom a mixture of water and ammonia, thereby forming in the reaction zone a reaction medium; and
   (b) reacting a liquid polyethylene glycol in a heated reaction zone containing the reaction medium to form dioxane.

5. A method according to claim 4 wherein the liquid polyethylene glycol is continuously fed to the heated reaction zone in step (b).

6. A method according to claim 4 wherein the liquid polyethylene glycol used in step (a) comprises one or more members of the class of polyethylene glycols having the formula $H(OCH_2CH_2)_nOH$, wherein n is an integer from 2 to 7.

7. A method according to claim 4 wherein the liquid polyethylene glycol used in step (a) is diethylene glycol.

8. A method according to claim 4 wherein the mole ratio of ammonium dihydrogen phosphate to polyethylene glycol in step (a) is in the range from 0.8:1 to 12:1.

9. A method according to claim 4 wherein the reaction temperature during step (a) is in the range from 190° to 225° C.

10. A method according to claim 4 wherein the liquid polyethylene glycol feed in step (b) comprises one or more members of the class of polyethylene glycols having the formula $H(OCH_2CH_2)_nOH$, wherein n is at least 2.

11. A method according to claim 4 wherein the liquid polyethylene glycol feed in step (b) is a mixture of polyethylene glycols having an average molecular weight in the range of from about 200 to about 300.

12. A method according to claim 4 wherein the reaction medium comprises a mixture of partial phosphate esters of a polyethylene glycol, and ammonium salts of partial esters of a polyethylene glycol.

13. A method according to claim 4 wherein the liquid polyethylene glycol feed in step (b) is different from the liquid polyethylene glycol used in step (a).

14. A method according to claim 4 wherein the reaction zone during step (b) is maintained at temperatures in the range of from about 225° to about 275° C.

15. A method of making dioxane comprising the steps of:
  (a) heating in a reaction zone a mixture of ammonium dihydrogen phosphate and a liquid polyethylene glycol, while distilling therefrom a mixture of water and ammonia, thereby forming in the reaction zone a reaction medium;
  (b) feeding a liquid polyethylene glycol to a heated reaction zone containing the reaction medium, while distilling from the reaction zone a crude volatile product composition comprising dioxane, 5-ethyl-2-methylpyridine, and water;
  (c) condensing the crude volatile product composition to form a condensate comprising dioxane, 5-ethyl-2-methylpyridine and water;
  (d) drying the condensate to form an organic layer comprising dioxane and 5-ethyl-2-methylpyridine; and
  (e) distilling off from the organic layer a fraction consisting essentially of dioxane.

16. A method according to claim 15 wherein the liquid polyethylene glycol used in step (a) comprises one or more members of the class of polyethylene glycols having the formula $H(OCH_2CH_2)_nOH$, wherein n is an integer from 2 to 7.

17. A method according to claim 15 wherein the mole ratio of ammonium dihydrogen phosphate to polyethylene glycol in step (a) is in the range from 0.8:1 to 12:1.

18. A method according to claim 15 wherein the reaction temperature during step (a) is in the range from 190° to 225° C.

19. A method according to claim 15 wherein the liquid polyethylene glycol feed in step (b) comprises one or more members of the class of polyethylene glycols having the formula $H(OCH_2CH_2)_nOH$, wherein n is at least 2.

20. A method according to claim 15 wherein the liquid polyethylene glycol feed in step (b) is a mixture of polyethylene glycols having an average molecular weight in the range of from about 200 to about 300.

21. A method according to claim 15 wherein the reaction medium comprises a mixture of partial phosphate esters of a polyethylene glycol, and ammonium salts of partial esters of a polyethylene glycol.

22. A method according to claim 15 wherein the reaction zone during step (b) is maintained at temperatures in the range of from about 225° to about 275° C.

* * * * *